US00PP29515P2

(12) United States Plant Patent
Noodelijk

(10) Patent No.: US PP29,515 P2
(45) Date of Patent: Jul. 17, 2018

(54) ***CELOSIA* PLANT 'TWISTED ORANGE'**

(50) Latin Name: *Celosia argentea*
Varietal Denomination: TWISTED ORANGE

(71) Applicant: Robert Noodelijk, Woubrugge (NL)

(72) Inventor: Robert Noodelijk, Woubrugge (NL)

(73) Assignee: Floritec Breeding BV (NL)

( * ) Notice: Subject to any disclaimer, the term of this patent is extended or adjusted under 35 U.S.C. 154(b) by 0 days.

(21) Appl. No.: 15/530,997

(22) Filed: Apr. 4, 2017

(51) Int. Cl.
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Annette H Para
(74) *Attorney, Agent, or Firm* — Cassandra Bright

(57) ABSTRACT

A *Celosia* plant named 'TWISTED ORANGE' is disclosed, characterized distinctive deep orange flowers on dense, sturdy plants. Plants are useful for outdoor ornamental purposes.

1 Drawing Sheet

Genus and species: *Celosia argentea.*
Variety denomination: 'Twisted Orange'.

BACKGROUND OF THE INVENTION

'TWISTED ORANGE' is a product of a breeding and selection program for ornamental *Celosia* cultivars with a cristata type inflorescence, suitable for vegetative propagation The new plant of the present invention comprises a new and distinct cultivar of *Celosia* plant.

'TWISTED ORANGE' is a seedling resulting from a crossing conducted in April 2013 with the seed parent *Celosia* 'Twisted', and an unpatented, proprietary pollen parent referred to as '08.8094'. The new and distinct cultivar was discovered and selected by the inventor, Robert Noodelijk in a research green house in Monster, the Netherlands during April 2014.

'TWISTED ORANGE' was first asexually reproduced by terminal vegetative cuttings at a research greenhouse in Monster, the Netherlands, October 2014 and has been asexually reproduced over an approximately two-year period. The new cultivar has been found to retain its distinctive characteristics through successive asexual propagations.

SUMMARY OF THE INVENTION

The following are the most outstanding and distinguishing characteristics of the new cultivar when grown under normal horticultural practices in Monster, the Netherlands.

1. Unique deep orange flower color.
2. Sturdy plant habit.
3. Dense, well branched plant.

COMPARISON WITH PARENT VARIETIES

'TWISTED ORANGE' is similar to the seed parent variety in most characteristics, however, the new variety differs in the following:

1. Flowers of the new variety are deep orange, flowers of 'Twisted' are magenta red.

2. Plant habit of the new variety is less upright than 'Twisted'.
3. The new variety produces more branches per plant than 'Twisted'.
4. The new variety has brighter green foliage than 'Twisted'.
5. The flower size (crest) of the new variety is smaller than that of 'Twisted'.

'TWISTED ORANGE' is similar to the pollen parent variety in most characteristics, however, the new variety differs in the following:

1. Flowers of the new variety are deep orange, flowers of the pollen parent are light red.
2. Plant height of the new variety is taller than the parent.
3. The new variety produces less branches per plant than the pollen parent.

COMPARISON WITH COMMERCIAL CULTIVAR

'TWISTED ORANGE' can be compared to the unpatented commercial variety 'Heirloom Orange Peach Cocksomb'. 'TWISTED ORANGE' is similar in some horticultural characteristics, however the new variety differs in the following:

1. The new variety is less than half the height of this comparator.
2. the new variety branches profusely, allowing for successful vegetative propagation.
3. Flower color of the new variety is deep orange; flower color of this comparator ranges inconsistently between orange and light red.
4. Plants of the new variety are much more vigorous, allowing for successful commercial vegetative propagation.

'TWISTED ORANGE' can be compared to the unpatented commercial variety 'Nana Jessica'. 'TWISTED ORANGE' is similar in some horticultural characteristics, however the new variety differs in the following:

1. The new variety produces a dense, flat comb, the comparator produces an irregular, globular comb.

2. The new variety branches profusely, allowing for successful commercial vegetative propagation.
3. Flower color of the new variety is deep orange; flower color of this comparator is orange mixed with light red.
4. Plants of the new variety are much more vigorous, allowing for successful commercial vegetative propagation.

DESCRIPTION OF THE PHOTOGRAPH

The present invention of a new and distinct variety of *Celosia* is shown in the accompanying photographs, the colors being as nearly true as possible with color photographs of this type. The photograph is of a plant that has been in bloom for approximately 3 weeks at approximately 16 weeks of age in a 15 cm pot.

DESCRIPTION OF THE INVENTION

This new variety of *Celosia* is of the botanical classification *Celosia argentea*. The observations and measurements were gathered from plants grown in a greenhouse in Monster, the Netherlands. No growth retardants were used. No tests were done on disease or insect resistance or susceptibility. No tests were done on cold or drought tolerance The following is a description of the plant and characteristics that distinguish 'TWISTED ORANGE' as a new and distinct variety. The color designations are taken from the plant itself. Accordingly, any discrepancies between the color designations and the colors depicted in the photographs are due to photographic tolerances. The color chart used in this description is The Royal Horticultural Society color chart, edition 1995.

DETAILED BOTANICAL DESCRIPTION

Classification:
- *Botanical.*—*Celosia argentea.*
- *Common name.*—Cockscomb, cristata flower type.
- *Denomination.*—'Twisted Orange'.

Plant:
- *Growth habit.*—Upright, slightly upwardly spreading annual.
- *Growth rate.*—Rapid.
- *Height.*—25.0 cm to 30.0 cm (with weekly growth retardant).
- *Width.*—15.0 cm to 20.0 cm (with weekly growth retardant).

Branches:
- *Stem.*—Color: Near RHS Yellow-Green 145B. Strength: Strong. Brittleness: Branches are not brittle. Anthocyanin coloration: Not present.
- *Length of lateral branch (from top to bottom).*—16.0 cm to 18.0 cm.
- *Diameter of lateral branch.*—0.8 cm.
- *Lateral branch color.*—Near RHS Yellow-Green 145B.
- *Lateral branch attachment.*—Alternate.
- *Branching.*—Average number of lateral branches: Prolific, with 6 to 8 breaks after pinching.
- *Auxiliary branch (when present).*—Length: Approximately 3.0 cm. Diameter: 0.3 cm. Color: RHS Yellow-Green 145B.

Foliage:
- *Color.*—Upper surface: Near RHS Green 137B. Lower surface: RHS Near RHS Yellow-Green 147B. Veins: Near RHS Yellow-Green 147B.
- *Size.*—
- *Mature foliage.*—Length: About 5 to 12.02 cm. Width: About 0.7 to 5.0 cm.
- *Quantity per lateral branch.*—12 to 16.
- *Shape.*—Cordiform.
- *Apex.*—Acuminate.
- *Base.*—Attenuate.
- *Margin.*—Entire.
- *Texture.*—Upper surface: Glabrous. Lower surface: Glabrous.
- *Venation arrangement.*—Pinnate.

Inflorescence: Fasciation at the tips of the majority of branches results in a colored crest that differs in size and form. Fasciation of the lateral branches results in large crests. Fasciation, when present on the auxiliary branches, results in much smaller crests or into a needle form, all with a hairy surface.
- *Type.*—Many small individual tubular flowers on a comb shaped inflorescence.
- *Size.*—1 week old crest: Bow width: 4.0 cm to 6.0 cm. Width of curled edge: 3.0 cm. 3 week old crest: Bow width: 7.0 cm to 9.0 cm. Width of curled edge: 4.0 cm to 5.0 cm. Size of crest of auxiliary branch (when present, no development of crest): Bow width: 2.5 cm to 3.5 cm. Width of curled edge: 1.0 to 1.5 cm. Size of needles of auxiliary branch (when present, no development of crest): Length: 2.0 cm to 4.0 cm. Diameter: 0.5 cm.
- *Number of combs per branch.*—Approximately 7 to 12 per branch.
- *Color of the crests.*—Mainly RHS 169A (greyed-orange) with a tiny RHS 168C (greyed-orange) line on the outer edge.
- *Number of blooms per crest.*—Usually 'Twisted Orange' is sterile, very rarely some blooms appear at the bottom of the crests or randomly at the surface of the crest.
- *Number of blooms when present.*—1 to 4.
- *Inflorescence lastingness on the plant (blooming period).*—10 weeks.
- *Fragrance.*—Absent.
- *Discoloration to color.*—None.
- *Peduncle.*—Length: 1.0 cm to 2.0 cm. Diameter: 0.3 cm. Color: RHS Green 141B.
- *Response time.*—7 to 8 weeks.

Ray florets (when present):
- *Number of petals per floret.*—5.
- *Petal texture (both surfaces).*—Papery, glabrous.
- *Apex.*—Acuminate.
- *Margin.*—Entire.
- *Length.*—0.5 cm.
- *Width.*—0.1 cm.
- *Color.*—(Both surfaces) — Near RHS Orange-Red 34B.

Reproductive organs:
- *Stamen.*—Width: Very thin, 0.3 cm. Color: Near RHS Red-Purple 62D. Pollen amount: Moderate. Pollen color: Near RHS Greyed-Orange 165C.
- *Pistil.*—Style appearance: Very fine, linear. Style color: Near RHS Greyed-Orange 170C. Style length: 0.6 cm. Stigma color: Near RHS Greyed-Orange 170C. Stigma width: 0.1 cm.

Other characteristics:

Fruit/seed set: Not observed.

Disease/pest resistance: Typical to known *Celosia* varieties. Neither resistance nor susceptibility to the normal diseases and pests of *Celosia* have been observed. Pests common to *Celosia* include Aphids and thrips. Typical diseases are *Botrytis* and *Pythium*.

Temperature tolerance: 5° C. to 38° C.

Drought tolerance: No tolerance for drought.

What is claimed is:

1. A new and distinct variety of *Celosia* plant named 'Twisted Orange' as described and shown herein.

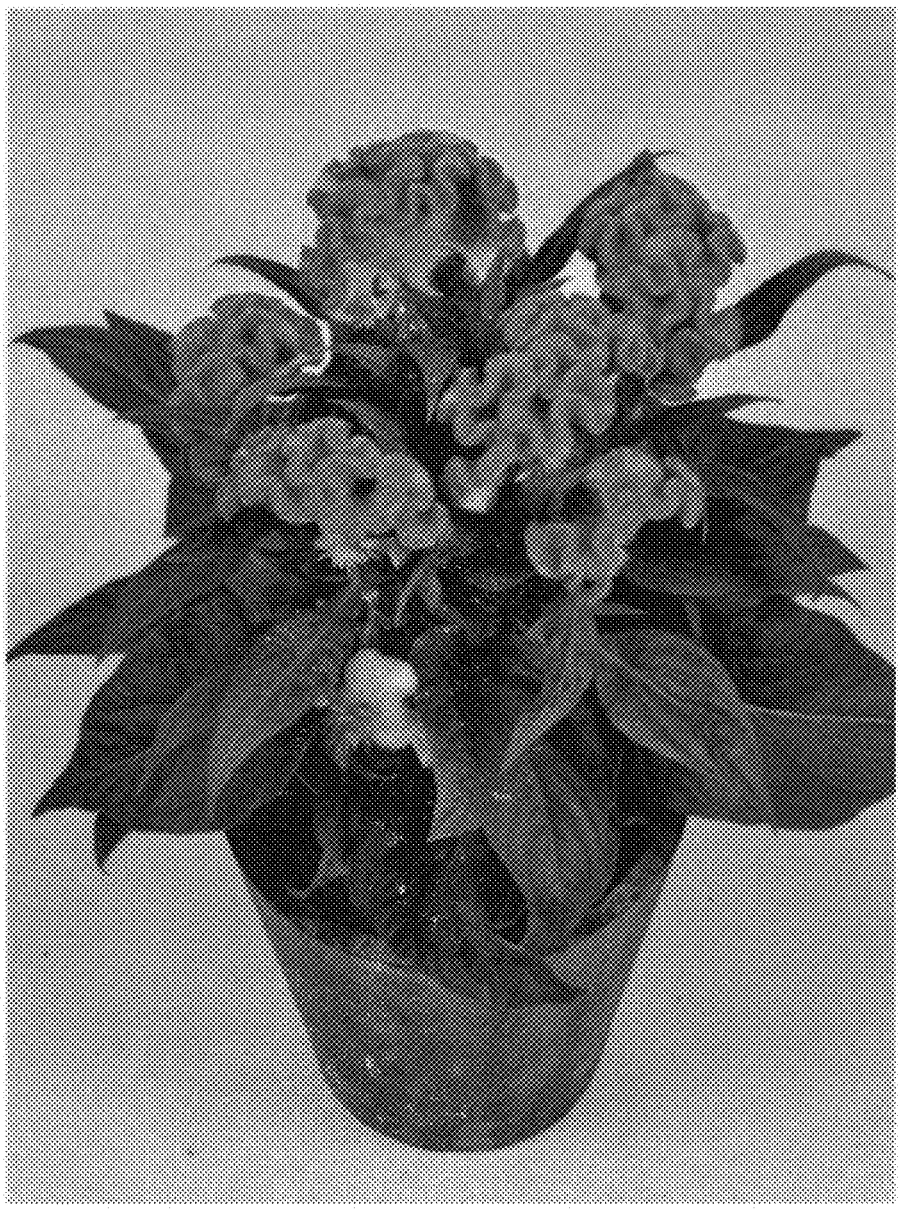

* * * * *